US00PP13157P2

(12) United States Plant Patent
Robertson

(10) Patent No.: US PP13,157 P2
(45) Date of Patent: Oct. 29, 2002

(54) ILEX PLANT NAMED 'FOSTER'S PURPLE GEM'

(75) Inventor: Phillip Bradford Robertson, Rock Spring, GA (US)

(73) Assignee: Burkhart Farms Nursery, Rock Spring, GA (US)

( * ) Notice: Subject to any disclaimer, the term of this patent is extended or adjusted under 35 U.S.C. 154(b) by 0 days.

(21) Appl. No.: 09/891,423

(22) Filed: Jun. 27, 2001

(51) Int. Cl.[7] ..... A01H 5/00

(52) U.S. Cl. ..... Plt./247

(58) Field of Search ..... Plt./247

*Primary Examiner*—Bruce R. Campell
*Assistant Examiner*—Anne Marie Grunberg
(74) *Attorney, Agent, or Firm*—C. A. Whealy

(57) ABSTRACT

A distinct cultivar of Ilex plant named 'Foster's Purple Gem', characterized by its upright and somewhat outwardly spreading growth habit; short internodes and very freely branching habit; dense and bushy plant habit; purple-colored young stems; small dark green-colored leaves; and very freely flowering habit.

3 Drawing Sheets

BACKGROUND OF THE INVENTION

The present Invention relates to a new and distinct cultivar of Ilex plant, botanically known as *Ilex×attenuata*, and hereinafter referred to by the name 'Foster's Purple Gem'.

le;2qThe new cultivar is a naturally-occurring branch mutation of the *Ilex×attenuata* cultivar Foster #2, not patented. The new cultivar was discovered and selected by the Inventor in a controlled environment in Rock Spring, Ga. in July, 1998. The new cultivar was primarily selected on the basis of its reduced leaf size.

Asexual reproduction of the new cultivar in a controlled environment by semi-hardwood cuttings taken in Rock Spring, Ga., since July, 1998, has shown that the unique features of this new Ilex are stable and reproduced true to type in successive generations.

SUMMARY OF THE INVENTION

Plants of the cultivar Foster's Purple Gem have not been observed under all possible environmental conditions. The phenotype may vary somewhat with variations in environment such as temperature, light intensity, daylength, humidity, water status and/or fertilizer rate and type without, however, any variance in genotype.

The following traits have been repeatedly observed and are determined to be the unique characteristics of 'Foster's Purple Gem'. These characteristics in combination distinguish 'Foster's Purple Gem' as a new and distinct cultivar:

1. Upright and somewhat outwardly spreading growth habit.

2. Short internodes and very freely branching habit, dense and bushy plant habit.

3. Purple-colored young stems.

4. Small dark green-colored leaves.

5. Very freely flowering habit.

Plants of the new Ilex are most similar to the parent cultivar, the cultivar Foster #2. However, in side-by-side comparisons conducted by the Inventor in Rock Spring, Ga., plants of the new Ilex differ from plants of the cultivar Foster #2 in the following characteristics:

1. Plants of the new Ilex are more compact than plants of the cultivar Foster #2.

2. Plants of the new Ilex are more freely branching, have shorter internodes and are denser than plants of the cultivar Foster #2.

3. Plants of the new Ilex have darker colored stems than plants of the cultivar Foster #2.

4. Plants of the new Ilex have much smaller and darker green leaves with fewer marginal spines than plants of the cultivar Foster #2.

5. Plants of the new Ilex root slower than plants of the cultivar Foster #2.

6. Plants of the Ilex produce more flowers but fewer drupes than plants of the cultivar Foster #2.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Ilex.

The photograph on the first sheet comprises a side perspective view of a typical flowering plant of 'Foster's Purple Gem'.

The photograph on the second comprises a close-up view of typical flowers and leaves of 'Foster's Purple Gem'.

The photograph at the top of the third sheet comprises a side perspective view of typical plants of 'Foster's Purple Gem' (left) and 'Foster #2' (right).

The photograph at the bottom of the third sheet comprises a close-up view of typical lateral branches of 'Foster's Purple Gem' (left) and 'Foster #2' (right).

DETAILED BOTANICAL DESCRIPTION

In the following description, color references are made to The Royal Horticultural Society Colour Chart except where general terms of ordinary dictionary significance are used. Plants used for the photographs and description were about three years old and were grown in 25.5-cm containers in an polyethylene-covered greenhouse during the winter and in an unshaded outdoor nursery for the remainder of the year in Rock Spring, Ga. During the production of the plants temperatures ranged from 10 to 100° F.

Botanical classification: *Ilex×attenuata* cultivar Foster's Purple Gem.

Parentage: Naturally-occurring branch mutation of *Ilex× attenuata* cultivar Foster #2, not patented.

Propagation:

*Type cutting.*—Semi-hardwood cuttings.

*Time to initiate roots, summer.*—About 60 days at 85° F.

*Time to initiate roots, winter.*—About 90 days at 45° F.

*Time to produce a rooted cutting, summer.*—About 90 days at 85° F.

*Time to produce a rooted cutting, winter.*—About 120 days at 45° F.

*Root description.*—Fine, fleshy, fibrous, white in color and freely branching.

Plant description:

*Form.*—Perennial evergreen flowering shrub; upright and somewhat outwardly spreading, conical.

*Plant height.*—About 94 cm.

*Plant diameter, widest point.*—About 52 cm.

*Branching habit.*—Very freely branching, lateral branches potentially developing at every node. Minimal pruning is required to maintain plant shape.

*Lateral branches.*—Length: About 65 cm. Diameter: About 7.5 mm. Internode length: About 2 cm. Shape: Cylindrical in cross-section. Strength: Strong. Texture: Young: Smooth, glabrous. Mature: Woody. Color: Young stems: Between 148A and 146A, overlain with dark purple, close to 187A. Mature stems: Closest to 199B.

*Foliage description.*—Leaves small, simple, long-persisting; alternate; numerous, densely foliated. Length: About 4.1 cm. Width: About 1.6 cm. Shape: Narrowly elliptic. Apex: Sharply acute. Base: Attenuate. Margin: Entire with about five sharp spines per margin. Venation pattern: Pinnate. Texture, upper and lower surface: Smooth, glabrous, leathery and durable. Luster: Upper surface, slightly glossy; lower surface, dull. Petiole length: About 3.5 mm. Petiole diameter: Less than 1 mm. Petiole texture, upper and lower surfaces: Smooth, glabrous. Color: Young leaves, upper surface: Darker than 146A. Young leaves, lower surface: Close to 147B. Fully expanded leaves, upper surface: Darker than 147A. Fully expanded leaves, lower surface: Close to 147B. Venation, upper surface: Same as lamina. Venation, lower surface: Midvein, close to 146A; lateral veins, close to 147A. Petiole: Close to 200B.

Flower description:

*Flower type and habit.*—Single rotate flowers; axillary; flowers face mostly outward. Flowers persistent. Very freely flowering, more than 100 flowers per lateral branch will develop during the flowering season.

*Natural flowering season.*—Late spring, April through May, in the southern United States; flowering continuous during this period.

*Flower longevity on the plant.*—About two to three weeks.

*Fragrance.*—None detected.

*Flowers.*—Appearance: Small; rounded. Diameter: About 7 mm. Depth (length): About 2.5 mm.

*Flower buds (just before opening).*—Length: About 2.5 mm. Diameter: About 2 mm. Shape: Oblong. Color: 145B to 145C.

*Petals.*—Quantity: Four per flower in a single whorl, not fused. Length: About 3 mm. Width: About 2.5 mm. Shape: Oblong. Apex: Rounded. Margin: Entire. Texture, upper and lower surfaces: Smooth, glabrous, waxy. Color: When opening, upper and lower surfaces: 145C to 145D. Fully opened, upper surface: 145D to close to white, 155D. Fully opened, lower surface: 145C to 145D.

*Sepals.*—Arrangement/appearance: Four per flower in a single whorl; fused. Length: Less than 1 mm. Width: Less than 1 mm. Calyx length: Less than 1 mm. Calyx diameter: About 2 mm. Shape: Triangular. Apex: Acute. Margin: Entire. Texture, upper and lower surfaces: Smooth, glabrous. Color, upper and lower surfaces: 144A.

*Peduncles.*—Length: About 3.5 mm. Diameter: About 1 mm. Angle: About 45° from vertical. Strength: Strong. Color: 144A.

*Pedicels.*—Length: About 1.5 mm. Diameter: Less than 1 mm. Angle: About 45° from vertical. Strength: Strong. Color: 144A.

*Reproductive organs.*—Stamens: Quantity: Four per flower. Filament length: About 1.5 mm. Filament color: Close to 155D. Anther shape: Roughly oblong. Anther length: Less than 1 mm. Anther color: Close to 155D. Pollen: None observed. Pistils: Quantity: One. Pistil length: About 2 mm. Style length: About 1.5 mm. Styles diameter: About 1 mm. Style color: Close to 146A. Stigma shape: Rounded, cap-like. Stigma color: Close to 144A. Ovary color: Close to 146A.

*Fruit.*—Type: Drupe. Length: About 6 mm. Diameter: About 6 mm Shape: Spherical. Texture: Smooth, glabrous. Color: Close to 45A to 46A.

*Seed.*—Quantity per fruit: About 4 to 6. Length: Less than 1 mm. Diameter: Less than 1 mm. Texture: Bony covering. Color: Tan.

Disease resistance: Plants of the new Ilex have not been noted to be resistant to pathogens common to Ilex.

Weather tolerance: Plants of the new Ilex have been observed to be tolerant to rain and wind and tolerant to temperatures from 10 to 100° F.

It is claimed:

1. A new and distinct cultivar of Ilex plant named 'Foster's Purple Gem', as illustrated and described.

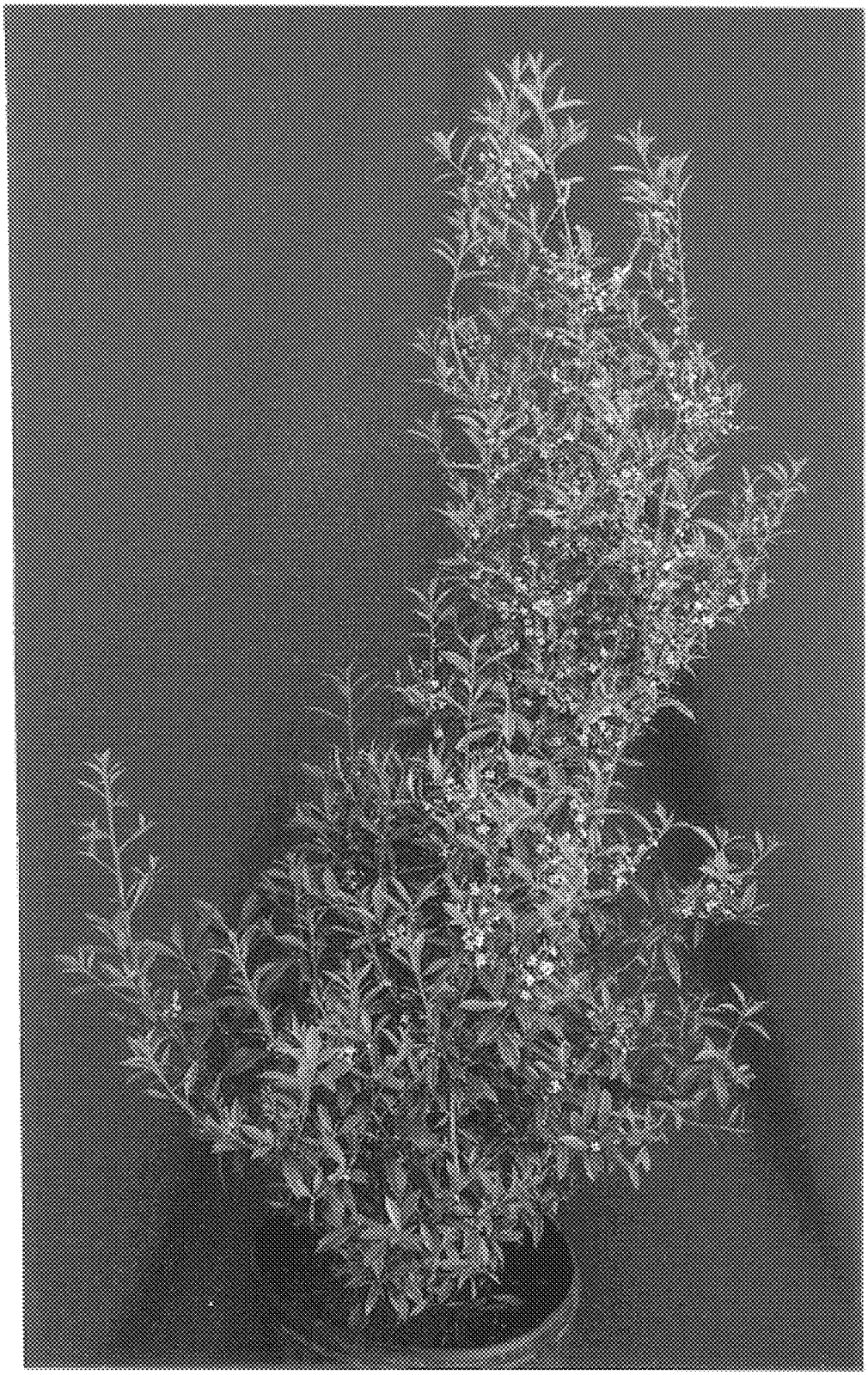

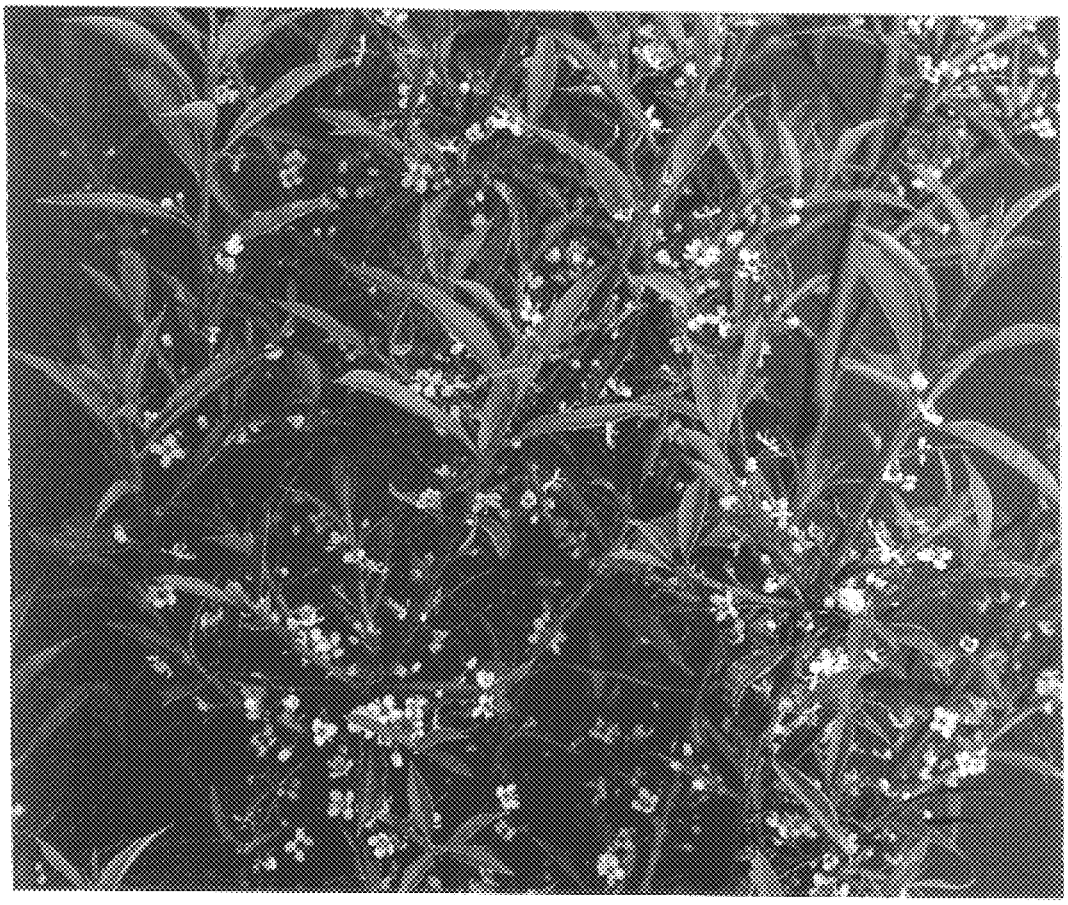

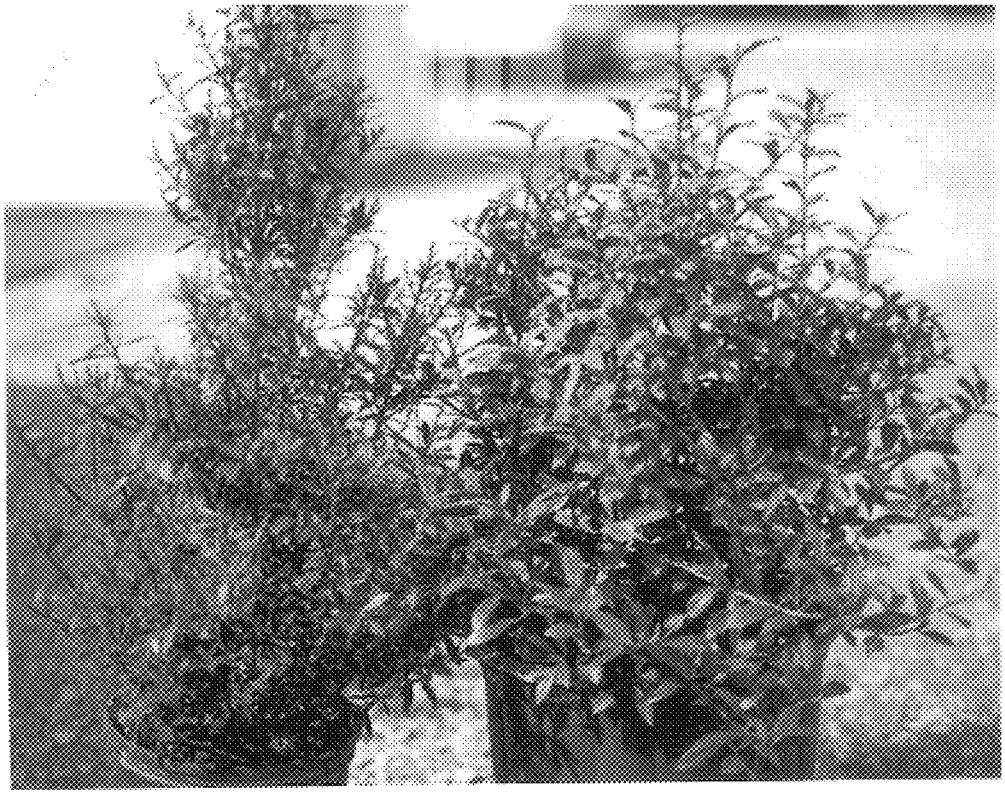
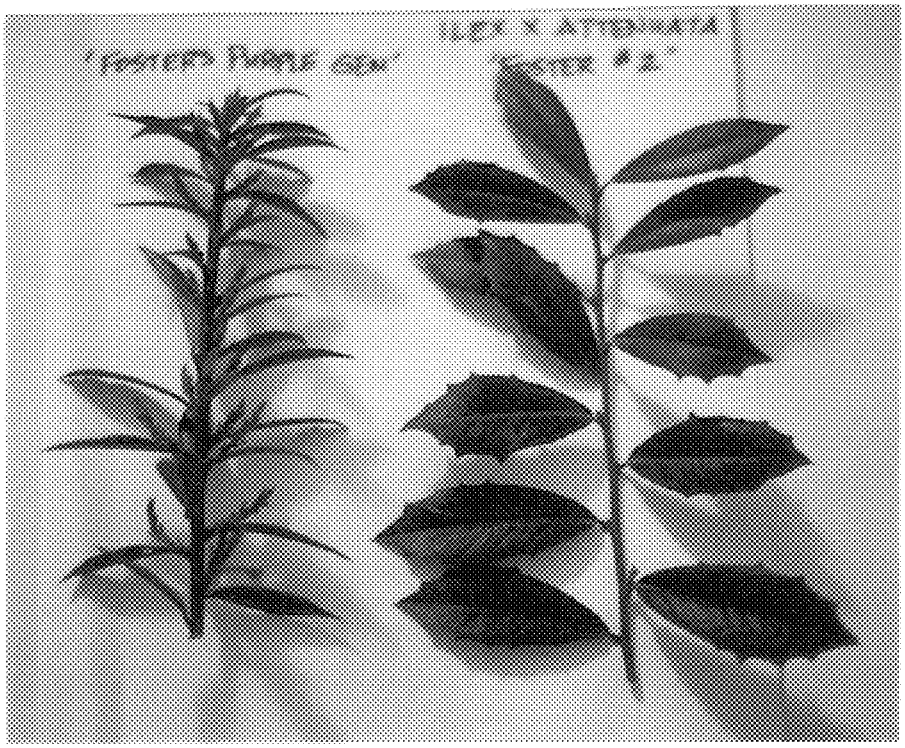

* * * * *